US006127076A

United States Patent [19]

Ishigami et al.

[11] Patent Number: 6,127,076

[45] Date of Patent: Oct. 3, 2000

[54] NAPHTHALENETETRACARBOXYLIC ACID DIIMIDE DERIVATIVES AND PHOTOSENSITIVE MATERIAL FOR ELECTROPHOTOGRAPHY

[75] Inventors: Kou Ishigami, Mishima; Fumio Sugai; Yasufumi Mizuta, both of Chuo-ku, all of Japan

[73] Assignee: Kyocera Mita Corporation, Osaka, Japan

[21] Appl. No.: 09/320,561

[22] Filed: May 27, 1999

[51] Int. Cl.[7] ............................ G03G 5/047; G03G 5/09

[52] U.S. Cl. ............................................ 430/58.5; 430/83

[58] Field of Search ............................ 430/58.5, 83, 900

[56] References Cited

U.S. PATENT DOCUMENTS

| | | | |
|---|---|---|---|
| 4,442,193 | 4/1984 | Chen et al. | 430/83 |
| 4,992,349 | 2/1991 | Chen et al. | 430/58.5 |
| 5,468,583 | 11/1995 | Gruenbaum et al. | 430/83 |
| 5,952,140 | 9/1999 | Visser et al. | 430/58.5 |

*Primary Examiner*—Roland Martin

[57] ABSTRACT

Naphthalenetetracarboxylic acid diimide derivatives represented by the following general formula, (1)

wherein R is a hydrogen atom, an alkyl group, an alkoxyl group or a halogen atom, R1 and R2 are different from each other and may be a substituted or unsubstituted alkyl group, alkoxyl group or an aryl group, respectively, and R3 is a hydrogen atom, a substituted or unsubstituted alkyl group, an alkoxyl group or an aryl group.

The derivatives exhibit excellent solubility in an organic solvent, excellent compatibility with a resin binder and excellent photosensitivity, and are very useful as an electron transporting agent for the electrophotosensitive material.

17 Claims, 3 Drawing Sheets

NAPHTHALENETETRACARBOXYLIC ACID DIIMIDE DERIVATIVES AND PHOTOSENSITIVE MATERIAL FOR ELECTROPHOTOGRAPHY

BACKGROUND OF THE INVENTION

1. Field of the Invention

The present invention relates to symmetrical naphthalenetetracarboxylic acid diimide derivatives and to a photosensitive material for electrophotography which contains a naphthalenetetracarboxylic acid diimide derivative as an electron transporting agent and is used for the electrophotographic copy, printer and common paper facsimile.

2. Description of the Prior Art

In an electrophotographic method, an electrophotosensitive material is electrically charged and is exposed to image-bearing light to form an electrostatic latent image which is, then, developed into a toner image in a state where a developing bias voltage is applied, and the formed toner image is transferred onto a transfer paper or the like paper and is fixed to form an image. This electrophotographic method is extensively used for the digital or analog copy, printer and common paper facsimile.

A selenium photosensitive material and an amorphous silicon photosensitive material have heretofore been used for the electrophotography. In recent years, however, an organic photosensitive material (OPC) has also been extensively used. Representative examples of the organic photosensitive material include a laminated-layer photosensitive material of the separated function type in which a charge-generating agent (CGM) and a charge-transporting agent (CTM) are laminated one upon the other as separate layers, and a single-layer photosensitive material in which the CGM and the CTM are formed as a single dispersion layer.

As the charge-generating agent, there have been known a variety of inorganic or organic charge-generating agents such as selenium, selenium-tellurium, amorphous silicon, pyrylium salt, azo pigment, disazo pigment, trisazo pigment, anthanthrone pigment, phthalocyanine pigment, indigo pigment, threne pigment, toluidine pigment, pyrazoline pigment, pyranthrone pigment, perylene pigment and quinacridone pigment. As the charge-transporting agent, there have been known positive hole-transporting agents such as poly-N-vinylcarbazole, phenanthrene, N-ethylcarbazole, 2,5-diphenyl-1,3,4-oxadiazole, 2,5-bis-(4-diethylaminophenyl)-1,3,4-oxadiazole, bis-diethylaminophenyl-1,3,6-oxadiazole, 4,4'-bis(diethylamino)-2,2'-dimethyltriphenylmethane, 2,4,5-triaminophenylimidazole, 2,5-bis(4-diethylaminophenyl)-1,3,4-triazole, 1-phenyl-3-(4-diethylaminostyryl)-5-(4-diethylaminophenyl)-2-pyrazoline, p-diethylaminobenzaldehyde-(diphenylhydrazone), tetra(m-methylphenyl) methaphenylenediamine, N,N,N',N'-tetraphenylbenzidine derivative, N,N'-diphenyl-N,N'-dixylylbenzidine, as well as electron-transporting agents such as 2-nitro-9-fluorenone, 2,7-dinitro-9-fluorenone, 2,4,7-trinitro-9-fluorenone, 2,4,5,7-tetranitro-9-fluorenone, 2-nitrobenzothiophene, 2,4,8-trinitrothioxanthone, dinitroanthracene, dinitroacridine, dinitroanthraquinone, naphthoquinones, and 3,5-dimethyl-3',5'-di-t-butyldiphenoquinone.

U.S. Pat. No. 4,442,193 discloses a photoconducting composition containing a photoconducting material and a 1,4,5,8-naphthalenebisdicarboxyimide derivative sensitizing compound.

U.S. Pat. No. 5,468,583 discloses a photoconducting element comprising an electrically conducting layer, a charge-generating layer and an electron-transporting agent in a polymeric binder layer, wherein the electron-transporting agent comprises at least one kind of a cyclic bisdicarboxyimide represented by the following formula (2), (2)

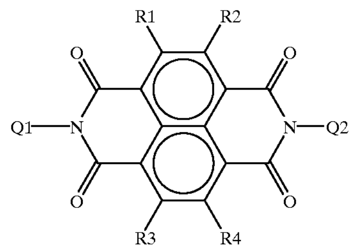

wherein Q1 and Q2 may be the same or different and are each a branched-chain alkyl group, an unsubstituted straight-chain alkyl group, an unsubstituted cyclic alkyl group, an alkyl-substituted cyclic alkyl group, an unsubstituted straight-chain unsaturated alkyl group, an aryl group, an alkyl group having 2 to 20 carbon atoms, an alkoxyl group or a hydrogen atom, and wherein Q1 and Q2 are not hydrogen atoms simultaneously, and R1, R2, R3 and R4 may be the same or different and are each a hydrogen atom, an alkyl group having 1 to 4 carbon atoms, an alkoxyl group having 1 to 4 carbon atoms, or a halogen atom.

Japanese Examined Patent Publication (Kokoku) No. 39098/1989 discloses an electric semiconductor or a photoconductor comprising naphthalenetetracarboxylic acid diimides represented by the following formula (3)

(3)

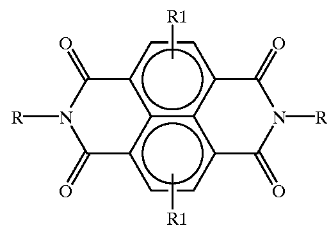

wherein R is a saturated or olefinically unsaturated aliphatic or alicyclic group which includes an electron-donating group, and R1, independently from each other, is a hydrogen atom, an alkyl group having 1 to 4 carbon atoms, a halogen atom, $NO_2$, $SO_3H$, CN, $COOR_2$, $NR_2$ (wherein $R_2$ is a hydrogen atom or an alkyl group having 1 to 4 carbon atoms), a hydroxyl group or an alkoxyl group having 1 to 4 carbon atoms.

Among the charge-transporting agents, however, very few electron-transporting agents are satisfying a practicable level, and further improvement in the performance is desired even with respect to photosensitivity.

The naphthalenetetracarboxylic acid diimide derivative is a promising compound as an electron-transporting agent but is not still satisfactory concerning solubility in an organic solvent and compatibility with a resin binder that is used, and tends to be precipitated in the form of crystals in the photosensitive layer and in the electron-transporting layer, deteriorating the electrophotographic properties of the photosensitive material.

When used at a concentration that maintains compatibility with the resin, furthermore, the naphthalenetetracarboxylic acid diimide derivative exhibits insufficient photosensitivity. It is therefore desired to increase its photosensitivity.

SUMMARY OF THE INVENTION

The present inventors have studied naphthalenetetracarboxylic acid diimide derivatives having excellent solubility in organic solvents, excellent compatibility with a resin binder that is used, and enhanced photosensitivity, have succeeded in synthesizing naphthalenetetracarboxylic acid diimide derivatives having a symmetrical structure as will be described below in detail, and have discovered the fact that the symmetrical naphthalenetetracarboxylic acid diimide derivatives exhibit excellent electron transporting property and photosensitivity, as well as excellent solubility in organic solvents and excellent resistance against being precipitated in a crystalline form.

It is therefore an object of the present invention to provide naphthalenetetracarboxylic acid diimide derivatives that exhibit excellent solubility in an organic solvent, excellent compatibility with a resin binder that is used, and excellent photosensitivity.

Another object of the present invention is to provide an organic photosensitive material for electrophotography containing a novel electron-transporting agent and having a high photosensitivity and a low residual potential and, as a result, capable of stably forming a highly dense vivid image without background fogging for extended periods of time.

According to the present invention, there are provided naphthalenetetracarboxylic acid diimide derivatives represented by the following general formula (1), (1)

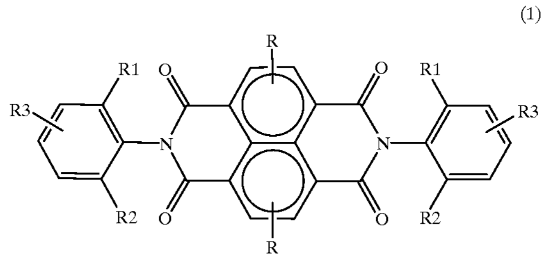

wherein R is a hydrogen atom, an alkyl group, an alkoxyl group or a halogen atom, the alkyl group and the alkoxyl group having or not having a subsituent, R1 and R2 are different from each other and are a substituted or unsubstituted group selected from the group consisting of an alkyl group, alkoxyl group and an aryl group, and R3 is a hydrogen atom, a substituted or unsubstituted alkyl group, an alkoxyl group or an aryl group, the alkoxyl group and the aryl group having or not having a subsituent.

According to the present invention, furthermore, there is provided a photosensitive material for electrophotography containing the above-mentioned naphthalenetetracarboxylic acid diimide derivatives.

It is desired that the photosensitive material for electrophotography further contains an electron acceptor in addition to the naphthalenetetracarboxylic acid diimide derivatives.

DETAILED DESCRIPTION OF THE INVENTION

Figure 1:
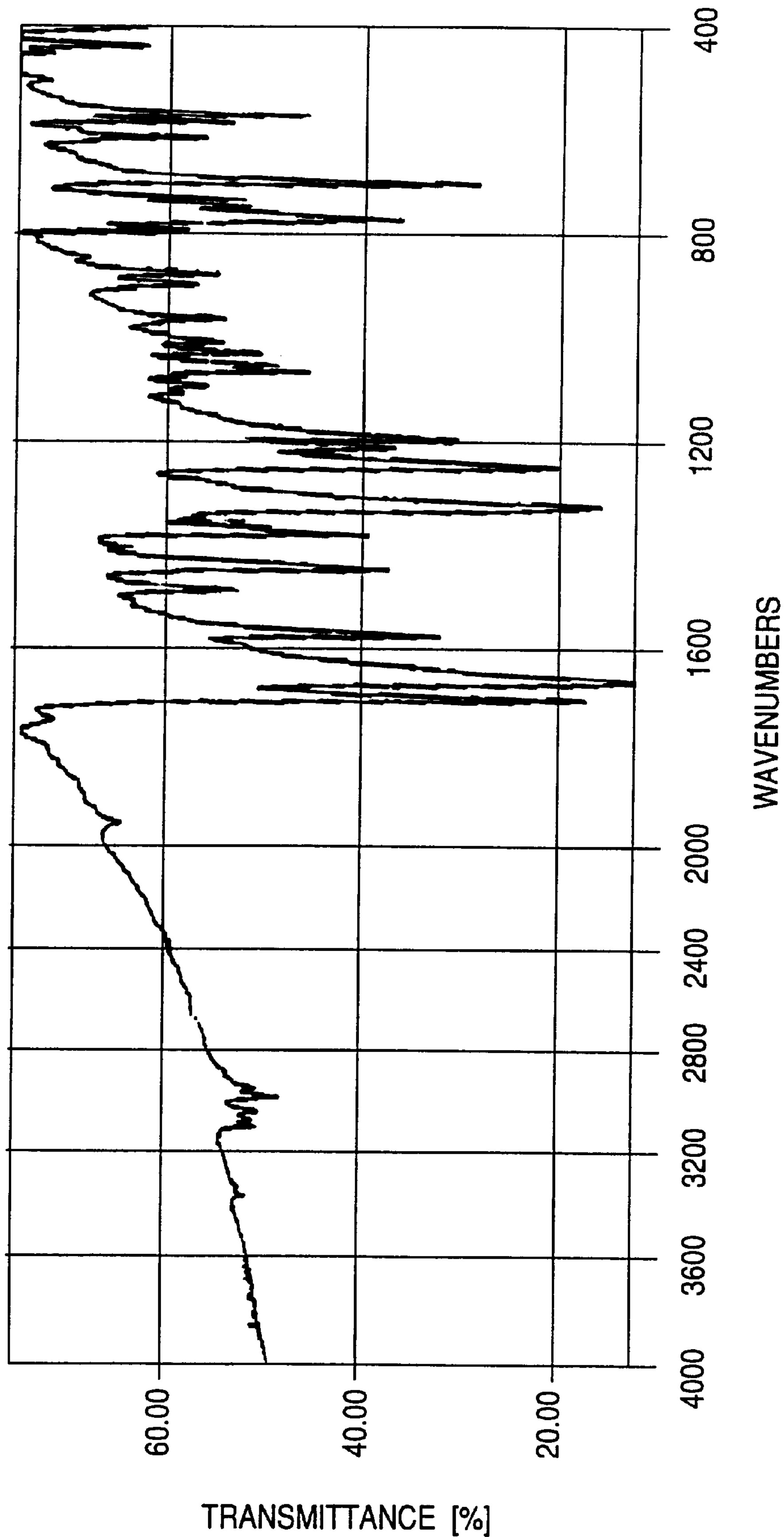
FIG. 1 shows an infrared-ray absorption spectrum of a naphthalenetetracarboxylic acid diimide derivative (Synthesis Example 1) according to the present invention.

The naphthalenetetracarboxylic acid diimide derivatives of the present invention have a structural feature in that substituents such as alkyl groups which are different from each other are attached to both ortho positions of a phenyl group bonded to both nitrogen atoms on a 1,4,5,8-naphthalenetetracarboxylic acid diimide skeleton as represented by the above-mentioned formula (1).

Reference should be made to Examples appearing later. That is, in Examples appearing later, a post-exposure potential (the smaller the potential, the higher the sensitivity) of the photosensitive material containing a charge-generating agent and an electron-transporting agent after it is irradiated with a ray of light of a predetermined optical intensity for a predetermined period of time, is used as an index of photosensitivity in order to evaluate the photosensitivity as well as to evaluate the presence of crystallization when the photosensitive material is blended in a resin.

The results teach unexpected facts that the naphthalenetetracarboxylic acid diimide derivatives of the present invention are crystallized in greatly suppressed amounts in the resin and exhibit strikingly increased photosensitivity compared with bis(N,N'-2-ethoxyethyl) naphthalenetetracarboxylic acid diimides.

According to the photosensitive material of the present invention, furthermore, the residual potential after the exposure to light is lowered, making it possible to form a charge image maintaining a high contrast as well as to stably form images with little background fogging for extended periods of time without disadvantage caused by the accumulation of electric charge.

[Naphthalenetetracarboxylic Acid Diimide Derivatives]

The naphthalenetetracarboxylic acid diimide derivatives used in the present invention have a chemical structure expressed by the following formula (substantially the same as the above-mentioned formula (1), (4)

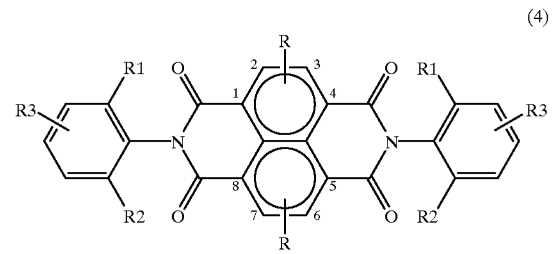

In these derivatives, substitutes such as alkyl groups (R1, R2) different from each other are bonded to both ortho positions of a phenyl group bonded to both nitrogen atoms of the naphthalenetetracarboxylic acid diimide skeleton. The naphthalenetetracarboxylic acid diimide derivatives of the present invention exhibit excellent solubility in organic solvents and excellent compatibility with a resin probably because the substituents such as alkyl groups which are different from each other are bonded to both ortho positions. It is further believed that these different substitutes are greatly contributing to improving the light absorbancy and electron transporting property.

The group R present in the compound is a hydrogen atom, an alkyl group, an alkoxyl group or a halogen atom. As an alkyl group, there can be exemplified an alkyl group with 1 to 6 carbon atoms, such as a methyl group, an ethyl group, an n-propyl group, an iso-propyl group, an n-butyl group, an iso-butyl group, a t-butyl group, an amyl group and a 2-ethylhexyl group. As an alkoxyl group, there can be exemplified a methoxyl group, an ethoxyl group, a propoxyl group and a butoxyl group having 1 to 4 carbon atoms. As a halogen atom, there can be exemplified a chlorine atom and a bromine atom.

R1 and R2 are each a substituted or unsubstituted alkyl group, an alkoxyl group or an aryl group. The alkyl group and alkoxyl group are those exemplified in connection with the group R. As the aryl group, there can be exemplified a phenyl group and a naphthyl group.

These groups (R1, R2) may not be substituted or may have a substituent such as alkyl group, alkoxyl group or halogen atom, and these substituents may be those described in connection with the group R. It is important that the groups R1 and R2 are different from each other. Under the condition in which R1 and R2 are different from each other, it is desired that R1 and R2 are each an alkyl group or an alkoxyl group with not more than 4 carbon atoms and, particularly, an alkyl group or an alkoxyl group with not more than 2 carbon atoms.

R3 is a hydrogen atom, an alkyl group, an alkoxyl group or an aryl group, and its concrete examples may be those exemplified above. (The alkyl group, the alkoxyl group and the aryl group may have a substituent.)

Either R1 or R2 may be the same as R3.

Concrete examples of the naphthalenetetracarboxylic acid diimide derivatives include:

N,N'-bis(2-ethyl-6-methylphenyl)naphthalene-1,4,5,8-tetracarboxylic acid diimide;

N,N'-bis(2,4-dimethyl-6-ethylphenyl)naphthalene-1,4,5,8-tetracarboxylic acid diimide;

N,N'-bis(2-methyl-6-ethylphenyl)naphthalene-1,4,5,8-tetracarboxylic acid diimide;

N,N'-bis(2-methyl-6-ethoxyphenyl)naphthalene-1,4,5,8-tetracarboxylic acid diimide;

N,N'-bis(2-methyl-6-methoxyphenyl)naphthalene-1,4,5,8-tetracarboxylic acid diimide; and N,N'-bis(2-methyl-6-methoxyethylphenyl)naphthalene-1,4,5,8-tetracarboxylic acid diimide.

The naphthalenetetracarboxylic acid diimide derivatives used in the present invention are not limited to the above-mentioned examples only, as a matter of course.

The above-mentioned naphthalenetetracarboxylic acid diimide derivatives are synthesized by reacting a naphthalenetetracarboxylic acid anhydride represented by he following formula (5), (5)

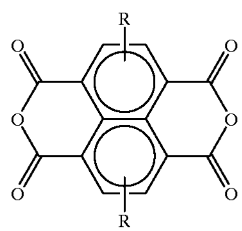

with primary amines (aniline derivatives) represented by the following formula (6), (6)

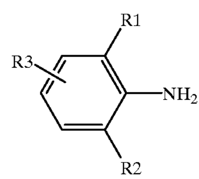

with refluxing.

As a solvent, it is desired to use a nonprotonic polar organic solvent such as dimethylformamide and dimethylacetamide. It is further desired that the reaction temperature is set to a boiling point of the solvent.

It is desired that the reaction is carried out by using a primary amine in an amount larger than a stoichiometric amount with respect to the naphthalenetetracarboxylic acid anhydride.

The naphthalenetetracarboxylic acid diimide derivatives of the present invention have an advantage of exhibiting excellent solubility in a solvent and excellent compatibility with the resin yet having a symmetrical structure. In general, the naphthalenetetracarboxylic acid diimide derivatives having asymmetrical structures exhibit superior solubility in the solvent to those having symmetrical structures. However, the naphthalenetetracarboxylic acid diimide derivatives having asymmetric structures require the use of primary amines A and B of different kinds. As a result, there are by-produced naphthalenetetracarboxylic acid diimide derivatives of the A—A type and the B—B type in addition to those of the A—B type, causing the yield to decrease and requiring cumbersome operation for the separation.

On the other hand, the naphthalenetetracarboxylic acid diimide derivatives of the symmetrical structure do not form such by-products though there may be contained conformational isomers, and, hence, offer advantages in the yield and purity. It is very meaningful that there are synthesized naphthalenetetracarboxylic acid diimide derivatives of the symmetrical structure exhibiting excellent solubility.

[Electrophotosensitive Materials]

The electrophotosensitive material of the present invention may be any photosensitive material provided it contains the above-mentioned naphthalenetetracarboxylic acid diimide as an electron-transporting agent and may, for example, be a single dispersion-type photosensitive material containing the electron-transporting agent (ETM) and the charge-generating agent (CGM) in a single photosensitive layer or a laminated-layer photosensitive material having the charge-generating layer (CGL) and the charge-transporting layer (CTL).

The composition of the photosensitive material will now be described.

(1) Charge-Generating Agents

As the charge-generating agent, there can be used, for example, selenium, selenium-tellurium, amorphous silicon, pyrylium salt, azo pigment, disazo pigment, anthanthrone pigment, phthalocyanine pigment, indigo pigment, threne pigment, toluidine pigment, pyrazoline pigment, perylene pigment and quinacridone pigment in one kind or in two or more kinds being mixed together so as to exhibit an absorption wavelength in a desired region.

The following phthalocyanine pigment, perylene pigment and bisazo pigment can be particularly preferably used.

Phthalocyanine pigment such as metal-free phthalocyanine, aluminum phthalocyanine, vanadium phthalocyanine, cadmium phthalocyanine, antimony phthalocyanine, chromium phthalocyanine, copper 4-phthalocyanine, germanium phthalocyanine, iron phthalocyanine, chloroaluminum phthalocyanine, oxotitanyl phthalocyanine, chloroindium phthalocyanine, chlorogallium phthalocyanine, magnesium phthalocyanine, dialkyl phthalocyanine, tetramethyl phthalocyanine, and tetraphenyl phthalocyanine. The crystalline form may be any one of α-type, β-type, γ-type, δ-type, ε-type, σ-type, χ-type or τ-type.

Perylene pigment represented by the general formula (7),

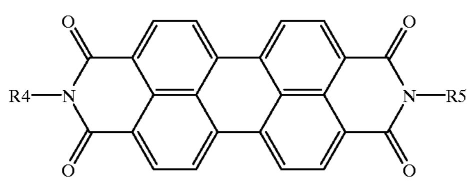

wherein R4 and R5 are each a substituted or unsubstituted alkyl group having not more than 18 carbon atoms, cycloalkyl group, aryl group, alkaryl group or aralkyl group.

Examples of the alkyl group include ethyl group, propyl group, butyl group and 2-ethylhexyl group, examples of the cycloalkyl group include cyclohexyl group and the like group, examples of the aryl group include phenyl group, naphthyl group, examples of the alkaryl group include tolyl group, xylyl group, ethylphenyl group, and examples of the aralkyl group include benzyl group and phenetyl group. Examples of the substituent include alkoxyl group and halogen atom.

Bisazo pigment represented by the following formula (8), $$Cp{-}N{=}N{-}Y{-}N{=}N{-}Cp \quad (8)$$

wherein Y is a divalent aromatic group that may include a heterocyclic group, and Cp is a coupler residue.

As the divalent aromatic group, there can be exemplified benzene, naphthalene, anthracene, phenanthrene, chrysene, anthraquinone, biphenyl, bisphenols, and a divalent group derived from a heterocyclic ring or a combination thereof. As the heterocyclic group, there can be exemplified monocyclic or polycyclic saturated or unsaturated heterocyclic rings having nitrogen, oxygen, sulfur or a combination thereof in the ring. Concrete examples include pyrrole, pyrazole, thiophene, furan, imidazoline, pyrimidine, pyrazoline, pyran, pyridine, benzofuran, benzoimidazoline, benzoxazole, indoline, quinoline, chromene, carbazole, dibenzofuran, xanthene and thioxanthene. These divalent groups may no be substituted or substituted. As the substituent, there can be exemplified alkyl group, aryl group and heterocyclic group. Here, examples of the alkyl group include methyl group, ethyl group, propyl group, butyl group and amyl group; examples of the aryl group include phenyl group, naphthyl group, biphenyl group, anthrile group, phenanthrile group and fluorenyl group; and examples of the substituted heterocyclic group include a monocyclic or polycyclic saturated or unsaturated heterocyclic group containing nitrogen, oxygen, sulfur or a combination thereof in the ring, such as thienyl group, furyl group, imidazolyl group, pyrrolyl group, pyrimidinyl group, imidazole group, pyradinyl group, pyrazolynyl group, pyrrolidinyl group, pyranyl group, piperidyl group, piperazinyl group, morpholyl group, pyridyl group, pyrimidyl group, pyrrolidinyl group, pyrrolinyl group, benzofuryl group, benzimidazolyl group, benzofuranyl group, indolyl group, quinolyl group, carbazolyl group and dibenzofuranyl group.

As the coupler residue in the formula (8), there can be used any residue of the coupler (azo coupling component) used for the azo pigment of this kind, such as substituted or unsubstituted phenols, naphthols or a hydroxyl group-containing heterocyclic ring compound. Here, as the substituent, there can be exemplified lower alkyl group, lower alkoxyl group, aryl group, acyloxyl group, halogen atom such as chloro, hydroxyl group, nitryl group, nitro group, amino group, amide group, acyloxyl group and carboxyl group.

(2) Charge-Transporting Agents

The charge-transporting agent used in the present invention contains the above-mentioned naphthalenetetracarboxylic acid diimide derivative as an electron-transporting agent. The derivative can be used alone as a charge-transporting agent, and can be further used in combination with a positive hole-transporting agent or an electron acceptor. The use in combination makes it possible to further enhance the photosensitivity.

As the positive hole-transporting material, the following compounds have been known and those that exhibit excellent solubility and positive hole-transporting property are selected out of them.

Pyrene,

N-ethylcarbazole,

N-isopropylcarbazole,

N-methyl-N-phenylhydrazino-3-methylindene-9-carbazole,

N,N-diphenylhydrazino-3-methylindene-9-ethylcarbazole,

N,N-diphenylhydrazino-3-methylindene-10-ethylphenothiazine,

N,N-diphenylhydrazino-3-methylindene-10-ethylphenoxazine, p-diethylaminobenzaldehyde-N,N-diphenylhydrazone, p-diethylaminobenzaldehyde-α-naphthyl-N-phenylhydrazone, p-pyrrolidinobenzaldehyde-N,N-diphenylhydrazone, 1,3,3-trimethylindolenine-ω-aldehyde-N,N-diphenylhydrazone, p-diethylbenzaldehyde-3-methylbenzthiazolinone-2-hydrazone, 2,5-bis(p-diethylaminophenyl)-1,3,4-oxadiazole, 1-phenyl-3-(p-diethylaminostyryl)-5-(p-diethylaminophenyl)pyrazoline, 1-[quinonyl(2)]-3-(p-diethylaminostyryl)-5-(p-diethylaminophenyl)pyrazoline, 1-[pyridyl(2)]-3-(p-diethylaminostyryl)- 5-(p-diethylaminophenyl)pyrazoline, 1-[6-methoxy-pyridyl(2)]-3-(p-diethylaminostyryl)-5-(p-diethylaminophenyl)pyrazoline, 1-[pyridyl(3)]-3-(p-diethylaminostyryl)-5-(p-diethylaminophenyl)pyrazolinel-[lepidyl(3)]-3-(p-diethylaminostyryl)-5-(p-diethylaminophenyl) pyrazoline, 1-[pyridyl(2)]-3-(p-diethylaminostyryl)-4-methyl-5-(p-diethylaminophenyl)pyrazoline, 1-[pyridyl(2)]-3-(α-methyl-p-diethylaminostyryl)-3-(p-diethylaminophenyl)pyrazoline, 1-phenyl-3-(p-diethylaminostyryl)-4-methyl-5-(p-diethylaminophenyl)pyrazoline, spiropyrazoline, 2-(p-diethylaminostyryl)-3-diethylaminobenzoxazole, 2-(p-diethylaminophenyl)-4-(p-dimethylaminophenyl)-5-(2-chlorophenyl)oxazole, 2-(p-diethylaminostyryl)-6-diethylaminobenzothiazole, bis(4-diethylamino-2-methylphenyl)phenylmethane, 1,1-bis(4-N,N-diethylamino-2-methylphenyl)heptane, 1,1,2,2-tetrakis(4-N,N-dimethylamino-2-methylphenyl)ethane, N,N'-diphenyl-N,N'-bis(methylphenyl)benzidine, N,N'-diphenyl-N,N'-bis(ethylphenyl)benzidine, N,N'-diphenyl-N,N'-bis(propylphenyl)benzidine, N,N'-diphenyl-N,N'-bis(butylphenyl)benzidine, N,N'-bis(isopropylphenyl)benzidine, N,N'-diphenyl-N,N'-bis(secondary butylphenyl)benzidine, N,N'-diphenyl-N,N'-bis(tertiary butylphenyl)benzidine, N,N'-diphenyl-N,N'-bis(2,4-dimethylphenyl)benzidine, N,N'-diphenyl-N,N'-bis(chlorophenyl)benzidine, triphenylamine, poly-N-vinylcarbazole, polyvinyl pyrene, polyvinyl anthracene, polyvinyl acridine, poly-9-vinylphenyl anthracene, pyrene-formaldehyde resin, and ethylcarbazole formaldehyde resin.

As a preferred positive hole-transporting agent, there can be exemplified aromatic amines represented by the following formula (9), (9)

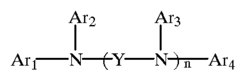

wherein Ar1, Ar2, Ar3 and Ar4 are substituted or unsubstituted aryl groups, Y is a substituted or unsubstituted arylene group, and n is a number of zero or 1.

As another preferred positive hole-transporting agent, there can be exemplified hydrazones and, particularly, hydrazones represented by the following formula (10), (10)

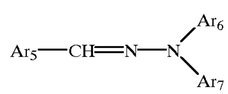

wherein Ar5, Ar6 and Ar7 are substituted or unsubstituted aryl groups.

As the electron acceptor used in combination with the naphthalenetetracarboxylic acid diimide derivative (electron-transporting agent) of the present invention, there can be used any one that has heretofore been used as the electron-transporting agent and, particularly, benzoquinones or naphthoquinones represented by the following formula (11), (11)

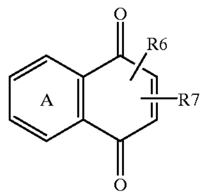

wherein a condensed ring A may be omitted, and R6 and R7 are hydrogen atoms, alkyl groups or acyloxyl groups, such as p-benzoquinone, 2,6-t-butylbenzoquinone, 1,4-naphthoquinone, 2-t-butyl-3-benzoyl-1,4-naphthoquinone, or 2-phenyl-3-benzoyl-1,4-naphthoquinone, and diphenoquinones represented by the following formula (12), (12)

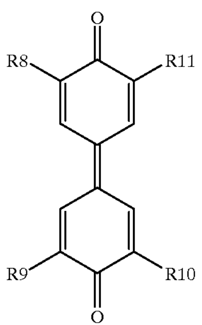

wherein R8, R9, R10, and R11 are alkyl groups, cycloalkyl groups, aryl groups or alkoxyl groups, which may be the same or different such as 3,5-dimethyl-3',5'-di-t-butyldiphenoquinone, 3,5-dimethoxy-3',5'-di-t-butyldiphenoquinone, 3,3'-dimethyl-5,5'-di-t-butyldiphenoquinone, 3,5'-dimethyl-3',5-di-t-butyldiphenoquinone, 3,5,3',5'-tetramethyldiphenoquinone, 2,6,2',6'-tetra-t-butyldiphenoquinone, 3,5,3',5'-tetraphenyldiphenoquinone, or 3,5,3',5'-tetracyclohexyldiphenoquinone.

(3) Binder Resins

As a resin medium for dispersing the charge-generating agent and the charge-transporting agent, there can be used a variety kinds of resins such as olefin polymers like styrene polymer, acrylic polymer, styrene-acrylic polymer, ethylene-vinyl acetate copolymer, polypropylene, and ionomer, and a variety kinds of polymers such as polyvinyl chloride, vinyl chloride-vinyl acetate copolymer, polyester, alkyd resin, polyamide, polyurethane, epoxy resin, polycarbonate, polyarylate, polysulfone, diallyl phthalate resin, silicone resin, ketone resin, polyvinyl butyral resin, polyether resin, phenol resin and photo-curing resins like epoxy acrylate. These binder resins can be used in one kind or in two or more kinds being mixed together. Preferred resins include styrene polymer, acrylic polymer, styrene-acrylic polymer, polyester resin, alkyd resin, polycarbonate and polyarylate.

Particularly preferred resins are a polycarbonate, Panlite manufactured by Teijin Kasei Co., PCZ manufactured by Mitsubishi Gas Kagaku Co., that pertain to a polycarbonate derived from bisphenols and phosgene, the polycarbonate is represented by the following general formula (13),

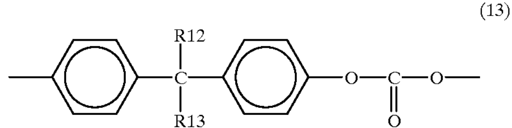

(13)

wherein R12 and R13 are hydrogen atoms or lower alkyl groups, and R12 and R13 being coupled together may form a cyclo ring such as a cyclohexane ring together with a carbon atom that is bonded thereto.

[Single-Layer Photosensitive Materials]

In the single-layer dispersion photosensitive material used in the present invention, it is desired that the charge-generating agent (CGM) is contained in the photosensitive layer in an amount of from 1 to 10% by weight and, particularly, from 3 to 5% by weight per the solid component, and that the naphthalenetetracarboxylic acid diimide derivative electron-transporting agent is contained in the photosensitive layer in an amount of from 3 to 100% by weight and, particularly, from 50 to 80% by weight per the solid component.

From the standpoint of photosensitivity and enabling the reversal development to be carried out (broadening the use), furthermore, it is desired to use the naphthalenetetracarboxylic acid diimide derivative electron-transporting agent (ET) and the positive hole-transporting agent (HT) in combination. In this case, the weight ratio of ET:HT is from 10:1 to 1:10 and, particularly, from 1:5 to 1:1.

When the naphthalenetetracarboxylic acid diimide derivative electron-transporting agent and the electron acceptor are used in combination, furthermore, the photosensitivity is further increased. In this case, it is desired that the electron-transporting agent and the electron acceptor are used at a weight ratio of from 1:1 to 10:1 to obtain enhanced photosensitivity by the addition in small amounts.

In the case of a single-layer photosensitive material, the thickness of the photosensitive layer is usually selected to be from 5 to 150 $\mu$m and, particularly, from 15 to 40 $\mu$m from the standpoint of electrophotographic properties.

[Laminated-Layer Photosensitive Materials]

In the case of the laminated-layer photosensitive material, it is desired that the charge-generating agent (CGM) is contained in an amount of from 5 to 1000 parts by weight and, particularly, from 30 to 500 parts by weight per 100 parts by weight of the solid resin component in the charge-generating layer (CGL) and that the naphthalenetetracarboxylic acid diimide electron-transporting agent is contained in an amount of from 0.1 to 40 parts by weight and, particularly, from 0.5 to 20 parts by weight per 100 parts by weight of the solid resin component in the charge-transporting layer (CTL).

In the case of the substrate/CGL/CTL photosensitive material, it is desired that the CGL lies over a range of, usually, from 0.01 to 5 $\mu$m and, particularly, from 0.1 to 3 $\mu$m and that the CTL lies over a range of from 2 to 100 $\mu$m and, particularly, from 5 to 50 $\mu$m.

[Preparation of the Photosensitive Materials]

The composition for forming the photosensitive material used in the present invention can be blended with various blending agents that have been known per se, such as antioxidant, radical-trapping agent, singlet quencher, UV-absorbing agent, softening agent, surface-reforming agent, defoaming agent, filler, viscosity-imparting agent, dispersion stabilizer, wax, acceptor and donor within a range in which they will not adversely affect the electrophotographic properties.

Upon blending at least the upper layer in the photosensitive material with a steric hindrant phenolic antioxidant in an amount of from 0.1 to 50% by weight per the total solid components, furthermore, the durability of the photosensitive material can be markedly improved without adversely affecting the electrophotographic properties.

As the electrically conducting substrate on which the photosensitive layer will be formed, there can be used various materials having electrically conducting property like a simple substance of a metal, such as aluminum, copper, tin, platinum, gold, silver, vanadium, molybdenum, chromium, cadmium, titanium, nickel, indium, stainless steel or brass, or a plastic material on which the above-mentioned metals are deposited or laminated, or a glass coated with aluminum iodide, tin oxide, or indium oxide. The photosensitive material of the present invention preferably employs an ordinary aluminum blank tube and, particularly, an aluminum blank tube coated with an alumite film maintaining a thickness of from 1 to 50 $\mu$m.

To form the photosensitive material, the charge-generating agent, electron-transporting agent and binder resin are used in combination, or the charge-generating agent and binder resin are used in combination, or the electron-transporting agent and binder resin are used in combination, thereby to prepare a coating composition relying upon a widely known method such as using a roll mill, ball mill, Atritor, paint shaker or ultrasonic dispersing device, and the coating composition is applied relying on a known coating means and is, as required, laminated followed by drying.

A variety of organic solvents can be used for forming a coating solution. Examples include alcohols such as methanol, ethanol, isopropanol and butanol; aliphatic hydrocarbons such as n-hexane, octane, and cyclohexane; aromatic hydrocarbons such as benzene, toluene and xylene; halogenated hydrocarbons such as dichloromethane, dichloroethane, carbon tetrachloride and chlorobenzene; ethers such as dimethyl ether, diethyl ether, tetrahydrofurane, ethylene glycol dimethyl ether, and diethylene glycol dimethyl ether; ketones such as acetone, methyl ethyl ketone and cyclohexanone; esters such as ethyl acetate and methyl acetate; and dimethylformamide and dimethylsulfoxide, which can be used in one kind or in two or more kinds being mixed together. The concentration of solid components in the coating solution is usually from 5 to 50%.

There is no particular limitation on the method of forming images by using the electrophotosensitive material of the present invention. Generally, the photosensitive material is electrically charged uniformly and is exposed to image-bearing light to form an electrostatic latent image. The electrostatic latent image is then developed by using a nonmagnetic one-component toner, a magnetic one-component toner, a magnetic two-component developing agent or a nonmagnetic two-component developing agent. The developed image is then transferred onto a transfer paper and is fixed thereby to form an image.

The present invention will now be described by way of Examples.

SYNTHESIS EXAMPLE 1

30 Parts by weight of a naphthalene-1,4,5,8-tetracarboxylic acid dianhydride and 35 parts by weight of 2-methyl-6-ethylaniline were heated in 100 parts by weight of dimethylformamide with refluxing for 3 hours. After cooled, the reaction mixture was filtered, the precipitate was washed with dimethylformamide and then with ether, followed by drying to obtain 48 parts by weight of N,N'-bis(2-methyl-6-ethylphenyl)naphthalene-1,4,5,8-tetracarboxylic acid diimide (decomposes at 270°) represented by the following formula (14),

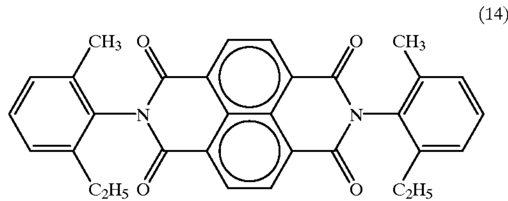

This compound is referred to as an electron transporting agent A.

Figure 2:
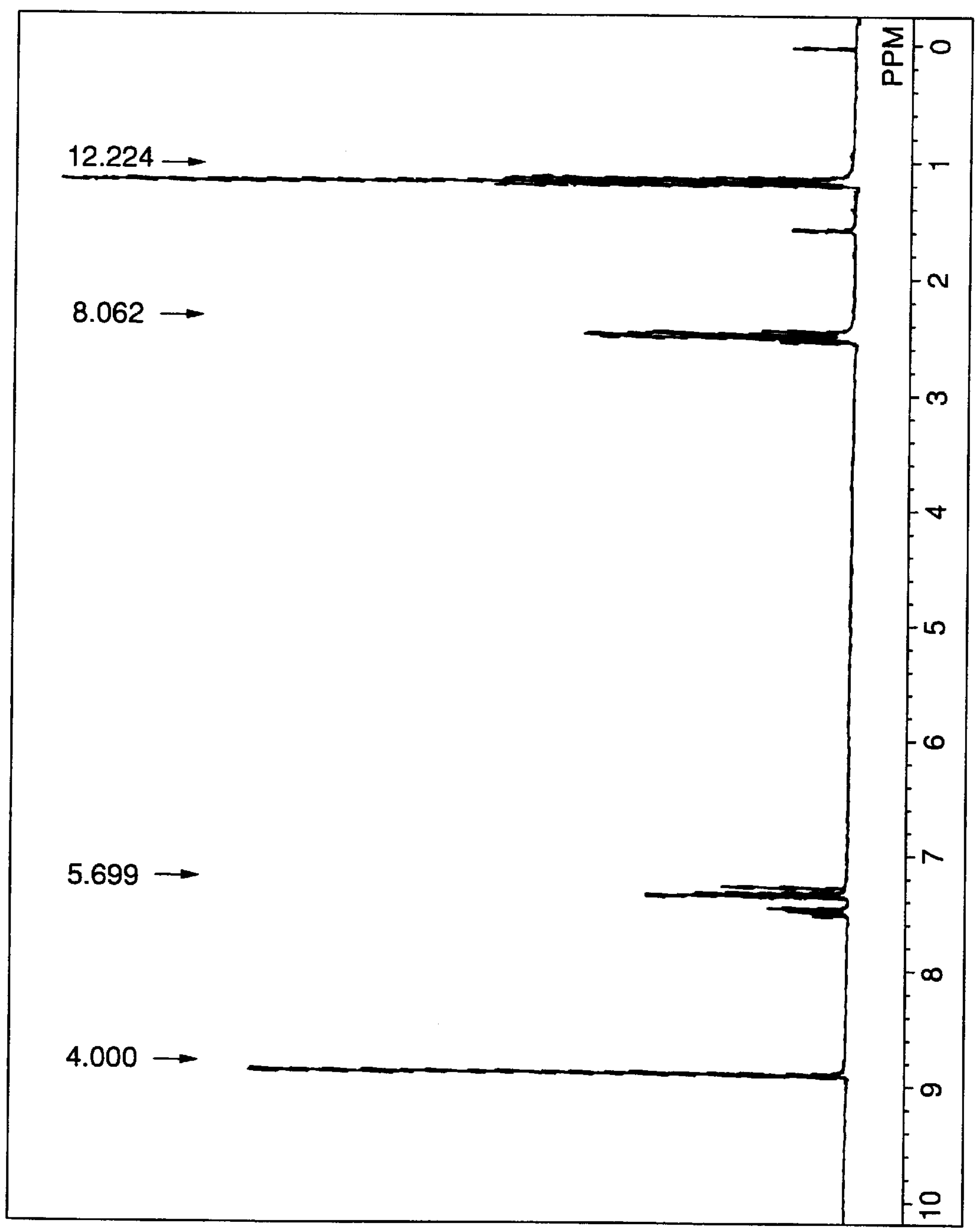
FIG. 2 shows a nuclear magnetic resonance spectrum of the naphthalenetetracarboxylic acid diimide derivative (Synthesis Example 1) according to the present invention.

FIG. 1 shows an infrared-ray absorption spectrum thereof, and FIG. 2 shows a nuclear magnetic resonance spectrum (NMR) thereof.

SYNTHESIS EXAMPLE 2

N,N'-bis(2-methyl-6-isopropylphenyl)naphthalene-1,4,5,8-tetracarboxylic acid diimide (decomposes at 250° C.) represented by the following formula (15),

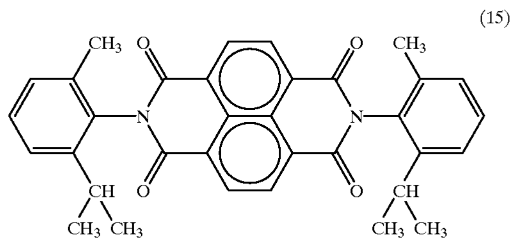

was synthesized in the same manner as in Synthesis Example 1 but using 2-methyl-6-isopropylaniline instead of 2-methyl-6-ethylaniline used in Synthesis Example 1.

Figure 3:
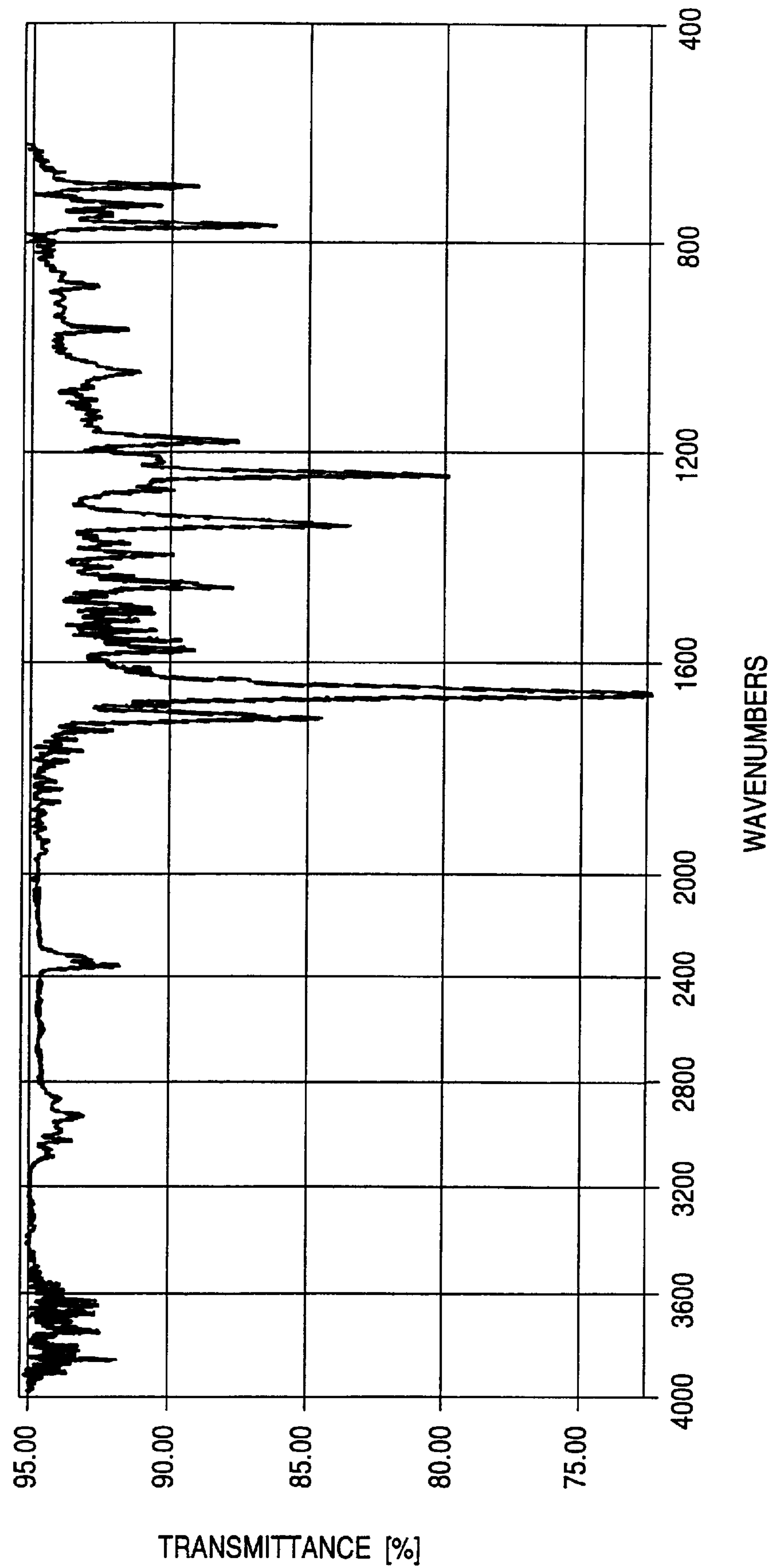
FIG. 3 shows an infrared-ray absorption spectrum of a naphthalenetetracarboxylic acid diimide derivative (Synthesis Example 2) according to the present invention.

FIG. 3 shows an infrared-ray absorption spectrum thereof. This compound is called an electron transporting agent A'.

Examples 1 to 9 and Comparative Examples 1 to 9

In the Examples, the above-mentioned electron transporting agent A was used.

In the Comparative Examples, N,N'-bis(2,6-dimethylphenyl)naphthalene-1,4,5,8-tetracarboxylic acid diimide derivative [electron transporting agent B] represented by the following formula (16) was used,

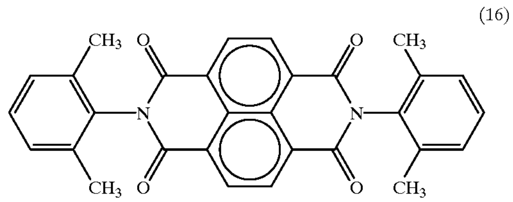

1. Preparation of Photosensitive Material.

(Single-Layer Photosensitive Material)

5 Parts by weight of a pigment shown in Table 1 as a charge-generating agent, 50 parts by weight of a compound shown in Table 1 as a positive hole-transporting agent, the amount shown in Table 1 of a compound shown in Table 1 as an electron-transporting agent, 100 parts by weight of a polycarbonate as a binder agent, and 800 parts by weight of a tetrahydrofuran as a solvent, were mixed and dispersed by using a ball mill for 50 hours to prepare a coating solution for forming a single-layer photosensitive layer. The thus prepared solution was then applied onto an aluminum blank tube and was dried with the hot air heated at 100° C. for 60 minutes to obtain a single-layer photosensitive material for electrophotography having a film thickness of from 15 to 20 μm.

(Laminated-Layer Photosensitive Material)

100 Parts by weight of a charge-generating agent, 100 parts by weight of a binder resin (polyvinyl butyral) and 2000 parts by weight of a solvent (tetrahydrofuran) were mixed and dispersed by the ball mill for 50 hours to prepare a coating solution for forming a charge-generating layer. The coating solution was then applied onto an aluminum blank tube and was dried with the hot air heated at 100° C. for 60 minutes to prepare a charge-generating layer having a film thickness of 1 μm.

Furthermore, the amount shown in Table 1 of an electron-transporting agent shown in Table 1, 100 parts by weight of a polycarbonate and 800 parts by weight of a solvent (toluene) were mixed and dispersed by using the ball mill for 50 hours to prepare a coating solution for forming a charge-transporting layer. The coating solution was then applied onto the charge-generating layer, and was dried with the hot air heated at 100° C. for 60 minutes to form a charge-transporting layer having a film thickness of 20 μm thereby to obtain a laminated-layer photosensitive material.

2. Evaluation.

(1) Method of Evaluating the Photosensitivity (in the case of a phthalocyanine pigment).

By using a drum sensitivity tester, a voltage was applied to the photosensitive materials obtained in Examples and in Comparative Examples to electrically charge them up to +700 V. Then, the photosensitive materials were irradiated on their surfaces with monochromatic light of 780 nm (half-value width, 20 nm) through a band-pass filter for a predetermined period of time, and the degrees of attenuation of the potential were observed to measure the electrophotographic properties.

Source of light: halogen lamp
Intensity of light: 16 $\mu W/cm^2$ (780 nm)
Irradiation time: 80 msec
Measurement of potential after exposed to light: 330 msec after the start of the exposure to light The results were as shown in Table 1.

In Table 1, the column Vr (V) shows surface potentials of the photosensitive materials 330 milliseconds after the start of the exposure to light.

(2) Method of Evaluating the Photosensitivity (in the case of a perylene pigment).

By using a drum sensitivity tester, a voltage was applied to the photosensitive materials obtained in Examples and in Comparative Examples to electrically charge them up to +700 V. Then, the photosensitive materials were irradiated on their surfaces with white light from a halogen lamp for a predetermined period of time, and the degrees of attenuation of the potential were observed to measure the electrophotographic properties.

Source of light: halogen lamp
Intensity of light: 147 $\mu W/cm^2$
Irradiation time: 50 msec
Measurement of potential after exposed to light: 330 msec after the start of the exposure to light The results were as shown in Table 1.

In Table 1, the column Vr (V) shows surface potentials of the photosensitive materials 330 milliseconds after the start of the exposure to light.

TABLE 1

| | Charge-generating agent | Positive hole-trans agent | Electron-transporting agent (parts by wt.) | Electron acceptor | Vr (V) | Remarks |
|---|---|---|---|---|---|---|
| Ex. 1 | $PcH_2$ | yes | A (30) | — | 185 | |
| Ex. 2 | PcTiO | yes | A (30) | — | 196 | |
| Ex. 3 (laminate) | $PcH_2$ | no | A (100) | — | 264 | |
| Ex. 4 | perylene type | yes | A (30) | — | 200 | |
| Ex. 5 (laminate) | perylene type | no | A (100) | — | 293 | |
| Ex. 6 | $PcH_2$ | yes | A (30) | a | 135 | |
| Ex. 7 | $PcH_2$ | yes | A (30) | b | 134 | |
| Ex. 8 | $PcH_2$ | yes | A (30) | c | 134 | |
| Ex. 9 | $PcH_2$ | yes | A (30) | d | 131 | |
| Comp. Ex. 1 | $PcH_2$ | yes | B (30) | — | 248 | crystallized |
| Comp. Ex. 2 | PcTiO | yes | B (30) | — | 245 | crystallized |
| Comp. Ex. 3 (laminate) | $PcH_2$ | no | B (100) | — | 345 | crystallized |
| Comp. Ex. 4 | perylene type | yes | B (30) | — | 296 | crystallized |
| Comp. Ex. 5 (laminate) | perylene type | no | B (100) | — | 375 | crystallized |
| Comp. Ex. 6 | $PcH_2$ | yes | B (30) | a | 245 | crystallized |
| Comp. Ex. 7 | $PcH_2$ | yes | B (30) | b | 242 | crystallized |
| Comp. Ex. 8 | $PcH_2$ | yes | B (30) | c | 237 | crystallized |
| Comp. Ex. 9 | $PcH_2$ | yes | B (30) | d | 230 | crystallized |

a: p-benzoquinone
b: 2,6-di-t-butylbenzoquinone
c: 3,5-dimethyl-3',5'-di-t-butyl-4,4'-diphenoquinone
d: 3,3',5,5'-tetra-t-butyl-4,4'-diphenoquinone
$PcH_2$: metal-free phthalocyanine
$PcTiO_2$: oxotitanyl phthalocyanine Examples 10 to 18

In Examples 10 to 18, use was made of the electron-transporting agent A' instead of the electron-transporting agent A used in Examples 1 to 18.

The results were as shown in Table 2 below.

TABLE 2

| | Charge-generating agent | Positive hole-trans agent | Electron-transporting agent (parts by wt.) | Electron acceptor | Vr (V) | Remarks |
|---|---|---|---|---|---|---|
| Ex. 10 | $PcH_2$ | yes | A' (30) | — | 185 | |
| Ex. 11 | PcTiO | yes | A' (30) | — | 197 | |
| Ex. 12 (laminate) | $PcH_2$ | no | A' (100) | — | 264 | |
| Ex. 13 | perylene type | yes | A' (30) | — | 201 | |
| Ex. 14 (laminate) | perylene type | no | A' (100) | — | 294 | |
| Ex. 15 | $PcH_2$ | yes | A' (30) | a | 137 | |
| Ex. 16 | $PcH_2$ | yes | A' (30) | b | 135 | |
| Ex. 17 | $PcH_2$ | yes | A' (30) | c | 133 | |
| Ex. 18 | $PcH_2$ | yes | A' (30) | d | 132 | |

What is claimed is:

1. An electrophotosensitive material comprising an electrically conducting substrate and an electrophotosensitive layer which contains a charge-generating agent and a charge-transporting agent; wherein said electrophotosensitive layer contains, as the charge-transporting agent, an electron-transporting agent which is naphthalenetetracarboxylic acid diimide derivatives represented by the following general formula (1)

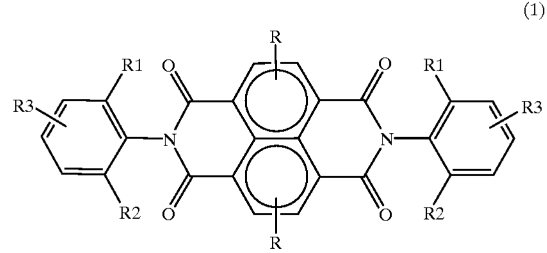

wherein R is a hydrogen atom, an alkyl group, an alkoxyl group or a halogen atom, the alkyl group and the alkoxyl group having or not having a substituent, R1 and R2 are different from each other and are a substituted or unsubstituted group selected from the group consisting of an alkyl group, an alkoxyl group and an aryl group, and R3 is a hydrogen atom, an alkyl group, an alkoxyl group or an aryl group, the alkyl group, the alkoxyl group and the aryl group having or not having a substituent.

2. An electrophotosensitive material according to claim 1, wherein said electrophotosensitive layer contains the electron-transporting agent in an amount of 50 to 80% by weight per the solid component.

3. An electrophotosensitive material according to claim 1, wherein said electrophotosensitive layer further contains a hole-transporting agent as the charge-transporting agent.

4. An electrophotosensitive material according to claim 1, wherein said electrophotosensitive layer is composed of a single layer in which the charge-generating agent and the charge-transporting agent are dispersed in a binder resin.

5. An electrophotosensitive material according to claim 1, wherein said electrophotosensitive layer is a laminate of a charge-generating layer containing the charge-generating agent and a charge-transporting layer containing the charge-transporting agent.

6. An electrophotosensitive material according to claim 1, wherein said groups R1 and R2 are alkyl groups having 1 to 4 carbon atoms or alkoxy groups having 1 to 4 carbon atoms.

7. An electrophotosensitive material comprising an electrically conducting substrate and an electrophotosensitive layer which contains a charge-generating agent and a charge-transporting agent; wherein said electrophotosensitive layer contains, as the charge-transporting agent, an electron-transporting agent which is naphthalenetetracarboxylic acid diimide derivatives represented by the following general formula (1):

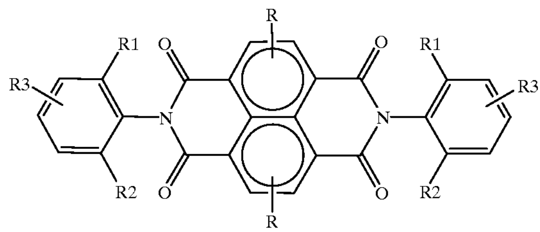

wherein R is a hydrogen atom, an alkyl group having 1 to 4 carbon atoms, or an alkoxy group having 1 to 4 carbon atoms, R1 and R2 are different from each other and are a group selected from the group consisting of an alkyl group having 1 to 4 carbon atoms and an alkoxyl group having 1 to 4 carbon atoms, and R3 is a hydrogen atom, an alkyl group having 1 to 4 carbon atoms or an alkoxyl group having 1 to 4 carbon atoms.

8. An electrophotosensitive material according to claim 7, wherein said electrophotosensitive layer is composed of a single layer in which the charge-generating agent and the charge-transporting agent are dispersed in a binder resin.

9. An electrophotosensitive material according to claim 7, wherein said electrophotosensitive layer is a laminate of a charge-generating layer containing the charge-generating agent and a charge-transporting layer containing the charge-transporting agent.

10. An electrophotosensitive material according to claim 7, wherein said groups R1 and R2 are alkyl groups having 1 to 4 carbon atoms.

11. An electrophotosensitive material according to claim 7, wherein said groups R1 and R2 are alkoxy groups having 1 to 4 carbon atoms.

12. An electrophotosensitive material comprising an electrically conducting substrate and an electrophotosensitive layer which contains a charge-generating agent and a charge-transporting agent; wherein said electrophotosensitive layer contains, as the charge-transporting agent, an electron-transporting agent which is naphthalenetetracarboxylic acid diimide derivatives represented by the following general formula (1):

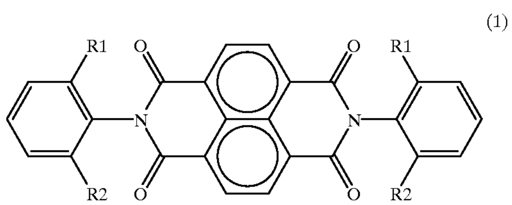

wherein R1 and R2 are different from each other and are a group selected from the group consisting of an alkyl group having 1 to 4 carbon atoms and an alkoxyl group having 1 to 4 carbon atoms.

13. An electrophotosensitive material according to claim 12, wherein said electrophotosensitive layer is composed of a single layer in which the charge-generating agent and the charge-transporting agent are dispersed in a binder resin.

14. An electrophotosensitive material according to claim 12, wherein said electrophotosensitive layer is a laminate of a charge-generating layer containing the charge-generating agent and a charge-transporting layer containing the charge-transporting agent.

15. An electrophotosensitive material according to claim 12, wherein said groups R1 and R2 are alkyl groups having 1 to 4 carbon atoms.

16. An electrophotosensitive material according to claim 12, wherein said groups R1 and R2 are alkoxy groups having 1 to 4 carbon atoms.

17. An e lectrophotosensitive material according to claim 1, further containing an electron acceptor.

* * * * *